United States Patent
Gokhale et al.

Patent Number: 5,256,783
Date of Patent: Oct. 26, 1993

[54] METHOD FOR PRODUCING 2-ISOQUINOLINE COMPOUNDS

[75] Inventors: Surendra Gokhale, Basel; Markus Schlageter, Bottmingen, both of Switzerland

[73] Assignee: Hoffmann-La Roche Inc., Nutley, N.J.

[21] Appl. No.: 938,750

[22] Filed: Sep. 2, 1992

[30] Foreign Application Priority Data

Sep. 18, 1991 [CH] Switzerland .......... 2752/91
Jul. 6, 1992 [CH] Switzerland .......... 2130/92

[51] Int. Cl.$^5$ .......................... C07D 217/16
[52] U.S. Cl. .......................... 546/146; 546/147
[58] Field of Search .......................... 546/146, 147

[56] References Cited

U.S. PATENT DOCUMENTS

| | | | |
|---|---|---|---|
| 3,836,536 | 9/1974 | Morrison et al. | 546/139 |
| 3,906,009 | 9/1975 | Farha, Jr. | 549/506 |
| 4,912,221 | 3/1990 | O'Reilly et al. | 546/147 |

OTHER PUBLICATIONS

Julian, *Journal of the American Chemical Society*, vol. 70, 1948, pp. 180–183.
Chrisey, *Heterocycles*, vol. 29, No. 4, Apr. 1, 1989, pp. 1179–1183.
March, *Advanced Organic Chemistry*, 3rd Ed., 1985 p. 495.
Database WPIL Week 9036, Derwent Publications Ltd., London, GB; AN 90-272653 and JP-A-02 193 969.

*Primary Examiner*—C. Warren Ivy
*Assistant Examiner*—Zinna N. Davis
*Attorney, Agent, or Firm*—George M. Gould; George W. Johnston; William Krovatin

[57] ABSTRACT

1,2,3,4-Tetrahydro-2-isoquinoline-derivatives of the formula

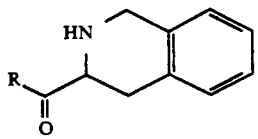

wherein R signifies hydroxy, lower alkylamino, lower alkoxy or phenyl-$C_{2-6}$-alkoxy which can carry one or more lower alkyl or lower alkoxy substituents on the phenyl ring, can be manufactured by cyclizing a phenethylamine derivative of the formula

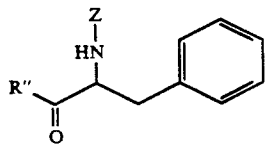

wherein Z signifies benzyloxycarbonyl and R" signifies hydroxy, lower alkylamino, lower alkoxy or phenyl-lower-alkoxy which can carry one or more lower alkyl or lower alkoxy substituents on the phenyl ring, with formaldehyde in the presence of sulphuric acid in acetic acid to a corresponding tetrahydroisoquinoline derivative of the formula

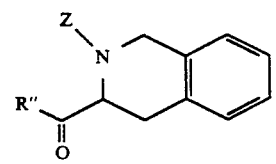

and cleaving off the group Z in the compound obtained.

11 Claims, No Drawings

METHOD FOR PRODUCING 2-ISOQUINOLINE COMPOUNDS

SUMMARY OF THE INVENTION

The present invention is a novel process for the manufacture of 1,2,3,4-tetrahydro-2-isoquinoline derivatives of the general formula

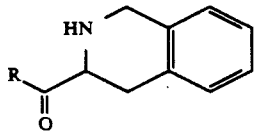

I wherein R signifies hydroxy, lower alkylamino, lower alkoxy or phenyl-$C_{(2-6)}$-alkoxy, the phenyl ring can be further substituted with one or more lower alkyl or lower alkoxy groups.

DESCRIPTION OF THE INVENTION

The term "lower alkyl" used in this description, alone or in combination, means straight-chain and branched alkyl groups with 1-6 carbons, preferably 1-4 carbons, some examples are methyl, ethyl, propyl, isopropyl, butyl, isobutyl, sec.-butyl, tert.-butyl, pentyl, hexyl and the like. The term "lower alkoxy" signifies lower alkyl ether groups in which the term "lower alkyl" has the same meaning as above, some examples of lower alkoxy are methoxy, ethoxy, propoxy, isopropoxy, butoxy, isobutoxy, sec.-butoxy, tert.-butoxy, pentyloxy, hexyloxy and the like. Similarly, the term "$C_{(2-6)}$-alkoxy" signifies alkyl ether groups with 2-6 carbon atoms.

The manufacture of compounds of formula I in which R signifies lower alkylamino is preferred. Isobutyamino or tert.-butylamino are preferred alkylamino groups with tert.-butylamino being more preferred.

The tetrahydroisoquinoline derivatives of formula I can be hydrogenated to the corresponding decahydroisoquinoline derivatives of the general formula

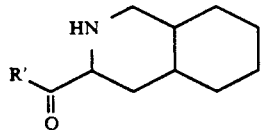

II wherein R' signifies hydroxy, lower alkylamino, lower alkoxy or cyclohexyl-$C_{(2-6)}$-alkoxy, the cyclohexyl ring can be further substituted with one or more lower alkyl or lower alkoxy groups.

These decahydroisoquinoline derivatives are valuable intermediates in the synthesis of protease inhibitors such as those which are described in EP-A 0,346,847 and 0,432,695. In particular, one of the decahydroisoquinoline derivatives of formula II, namely N-t-butyl-decahydro-(4aS,8aS)-isoquinoline-3(S)-carboxamide, is suitable for the manufacture of protease inhibitors of the general formula

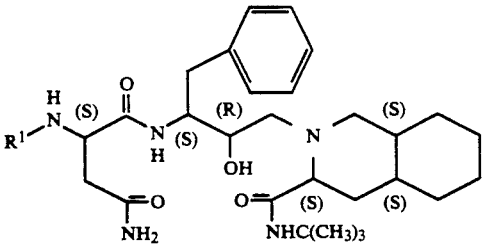

III wherein $R^1$ signifies benzyloxycarbonyl or 2-quinolycarbonyl, which are described in EP-A 0,432,695.

A conversion of the decahydroisoquinoline derivatives of formula II into the protease inhibitors of formula III is described in both EP-A 0,346,847 and 0,432,695.

The manufacture of tetrahydroisoquinoline derivatives by the Pictet-Spengler method starting from a phenethylamine derivative and formaldehyde in the presence of hydrochloric acid is known and as a practical matter is the only useful process for the manufacture of this class of substances. [See U.S. Pat. Nos. 3,836,536 and 3,906,009, European Patent Publications Nos. 0,012,845 and 0,029,488, (all of which refer to J. Amer. Chem. Soc. 70, 182 (1948)); See also European Patent Publications Nos. 0,018,104, 0,039,804 and 0,104,546, Heterocycles, 29, 6, (1989) 1179-1183]. This process is used even though it is generally known that two extremely carcinogenic α-haloethers, chloromethyl methyl ether (CMME) and bis(chloromethyl)methyl ether (BCME), are formed as byproducts in the Pictet-Spengler reaction by reaction of hydrochloric acid with formaldehyde [Chem. Rev. 55 (1955), 314]. The carcinogenity of these two α-haloethers, especially BCME, is so great that any process in which these compounds are formed as byproducts is not considered for industrial evaluation on safety grounds [Arch Environ Health, 30 (1975) 61-72].

A further disadvantage of the Pictet-Spengler synthesis arises in the cyclization of non-activated chiral phenethylamine derivates, wherein partial racemization can occur due to the rigorous reaction conditions; thus, as disclosed in Chem. Pharm. Bull. Japan 31, 312 (1983), about 32% racemization occurs in the synthesis of L-phenylalanine.

In accordance with Chem. Pharm. Bull Japan 25, 1732 (1977) non-activated systems such as 2-phenethylamine can be cyclized in the form of acyl derivatives (e.g. the tosyl derivative) under very mild reaction conditions using formaldehyde in the presence of boron trifluoride. Our experiments have shown that N-tosyl-(L)-phenylalanyl benzyl ester can be cyclized to the corresponding tetrahydroisoquinoline derivative without racemization using formaldehyde in the presence of boron trifluoride, but the cleavage of the tosyl group in the cyclization product is not optimal. It has also been possible to cyclize another acyl derivative of L-phenylalanine, namely N-benzyloxycarbonyl-L-phenylalanine t-butylamide to benzyl 3(S)-(t-butylcarbanoyl)-1,2,3,4-tetrahydro-2-isoquinolinecarboxylate without recemization using formaldehyde in the presence of boron trifluoride and to subsequently cleave off the benzyloxy group hydrogenolytically. However, problems arise with respect to the removal or recovery of boron compounds after the cyclization has been carried out because boron trifluoride, be it a complex with diethyl ether (which is problematical to process on an industrial scale), or a complex with acetic acid, must be used in a 1½- to 2-fold excess for the cyclization.

According to the present invention it has been found that phenethylamine derivatives of the general formula

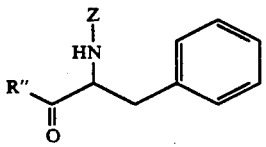

IV wherein Z signifies benzyloxycarbonyl and R" signifies hydroxy, lower alkylamino, lower alkoxy or phenyl-lower-alkoxy, the phenyl ring can be further substituted with one or more lower alkyl or lower alkoxy groups, can be cyclized using formaldehyde in good yield, without recemization and essentially without scale-up or safety problems to the correspondig tetrahydroisoquinoline derivatives of the general formula

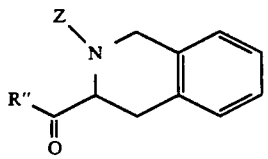

V wherein R' and Z have the same meaning as above, when the reaction is carried out in the presence of sulphuric acid in acetic acid.

The process in accordance with the invention accordingly comprises reacting a phenethylamine derivative of fromula IV with formaldehyde in the presence of sulphuric acid in acetic acid at a temperature between about room temperature and about 50° C. and subsequently cleaving off the group Z in the compound of formula V obtained. As used herein, room temperature is between 20°-25° C.

Paraformaldehyde or a suitable formaldehyde acetal, especially a di-lower-alkyl acetal such as dimethoxymethane, can be used in place of formaldehyde or an aqueous formaldehyde solution. The reaction temperature lies between about room temperature and 50° C., preferably between 45° and 50° C. when formaldehyde or paraformaldehyde is used. When dimethoxymethane is used, the reaction temperature should not exceed 40° C. (boiling point of dimethoxymethane: 41°-42° C.). The reaction takes place in a solvent which is inert under the reaction conditions, such as toluene, or in an excess of acetic acid, preferably in toluene. Depending on the precise reaction conditions, the reaction takes about 7 to about 24 hours. The best results are obtained when the phenethylamine derivative of formula IV is reacted in toluene with 3 molar equivalents of dimethoxymethane and 2 molar equivalents of 7.2M sulphuric acid in acetic acid for 24 and 25 hours at 40° C.

The cleavage of the benzyloxycarbonyl group (Z) from the cyclization product of formula V is conveniently effected hydrogenolytically, e.g. by hydrogenation in the presence of a palladium catalyst (such as 10% palladium-charcoal) in a solvent which is inert under the reaction conditions, e.g. in a lower alkanol such as ethanol or the like, whereby where R' signifies benzyloxy the benzyl group is likewise cleaved off hydrogenolytically and the corresponding compound of formula I in which R signifies hydroxy is obtained.

The reduction of the tetrahydroisoquinoline derivatives of formula I manufactured in accordance with the invention to the corresponding decahydroisoquinoline derivatives of formula II which are usable as valuable intermediates is conveniently effected by hydrogenation in the presence of a catalyst which is suitable for such hydrogenations, such as rhodium (conveniently 5% rhodium on Alox) or the like and in an organic solvent which is inert under the reaction conditions, such as ethyl acetate or the like, whereby a phenyl ring which may be present in the residue R is likewise hydrogenated.

The starting materials of formula IV are known or are readily accessible according to generally known methods; moreover, Example 1 hereinafter contains detailed information with respect to the preparation of such a starting material.

In the following Examples, which illustrate the present invention but are not intended to limit its scope in any manner, all temperatures are given in degrees Celsius.

EXAMPLE 1

A. 1000 g of N-benzyloxycarbonyl-L-phenylalanine were dissolved in 6400 ml of ethyl acetate. The solution was cooled to −2° (internal temperature) and treated dropwise with 438 g of 97 % N-ethylmorpholine under argon and while stirring within 45 minutes, whereby the internal temperature was held in a range of −1.8° to −0.6°. After adding 200 ml of ethyl acetate and stirring for 10 minutes 529 g of 95 % isobutyl chloroformate were added dropwise within 70 minutes and at an internal temperature of −1.8° to −0.6°, whereby a precipitate formed. After the addition of 200 ml of ethyl acetate the resulting suspension was stirred at −2° internal temperature for 30 minutes and then treated dropwise with 353 g of t-butylamine within 80 minutes, whereby the internal temperature was held in a range of −1.6° to −0.4°. After the addition of 200 ml of ethyl acetate the mixture was stirred at −2° internal temperature for a further 30 minutes, whereupon the suspension was left to warm to room temperature within 1 hour.

After adding 1400 ml of water and stirring at room temperature for 15 minutes two clear layers resulted and, after standing for 15 minutes, the yellowish aqueous phase (pH 7-8) was removed. 1000 ml of semi-saturated sodium bicarbonate solution were added to the organic phase, whereupon it was stirred vigourously for 15 minutes. The layers were left to separate for 15 minutes. the aqueous phase was removed, the organic phase was treated with 1000 ml of water, stirred for 15 minutes and the layers were left to separate for 15 minutes, whereupon the aqueous phase (pH≈7) was removed. The turbid organic phase was cooled in a bath of −15° while stirring slowly in order to freeze-out the residual moisture; at about −7° internal temperature crystallization of ice set in and the organic phase became clear; after stirring at −8° to −9° internal temperature for 5 minutes the ice was filtered off rapidly and there was obtained a clear ethyl acetate phase (about 9000 ml) which was concentrated under reduced pressure. After approximately 6000 ml of ethyl acetate had distilled off a viscous yellow oil began to separate, whereupon an argon atmosphere was again applied and the internal temperature was increased to 34°–40°.

8000 ml of hexane were added dropwise at an internal temperature of 43°–45°, whereby a clear slightly yellowish solution formed. This was cooled slowly (5°/hr.) to −5° and after cooling for a total of 16 hours the colourless solid was filtered off under suction at −5°. 1500 ml of hexane were used to wash the filter cake and also to rinse the flask in which the crystallization had been carried out. After drying the filter cake in a vacuum drying oven at 40° there were obtained 910 g (77%) of N-benzyloxycarbonyl-L-phenylalanine t-butylamide having a melting point of 99°–100°, purity (according HPLC) 99.6%, $[\alpha]_D^{20} = 4.9°$ (c=1 in methanol).

By concentration of the mother liquor there was obtained a yellow oil which was crystallized from 100 ml of t-butyl methyl ether and 500 ml of hexane, filtered off and washed with 50 ml of hexane/t-butyl methyl ether; there were obtained a further 83 g (7.3%) of N-benzyloxycarbonyl-L-phenylalanine t-butylamide of melting point 98°–100°, purity (according to HPLC) 99.0%. The total yield of N-benzyloxycarbonyl-L-phenylalanine t-butylamide was 84.3%.

B. 850.8 g of N-benzyloxycarbonyl-L-phenylalanine t-butylamide were dissolved in 3000 ml of toluene at room temperature. A previously prepared mixture of 240 ml of 95–97% sulphuric acid and 636 ml of 99.5% acetic acid was added dropwise to the turbid solution within 40 minutes while stirring, whereupon 547 g of dimethoxymethane were added within 30 minutes and the solution, which was still turbid, was warmed to 40° (internal temperature) for 24 hours.

After the addition of 1800 ml of toluene the reaction mixture was cooled to 15° and treated with 850 ml of 25% aqueous ammonia within 50 minutes at 15°–20° in order to buffer the system (to pH 8–8.5). 500 ml of water were added in order to dissolve the separated ammonium salt, whereupon the mixture was stirred at room temperature for 10 minutes and left to stand for 20 minutes. The aqueous phase was removed, whereupon the organic phase was treated with 1000 ml of water and the mixture was stirred at room temperature for 15 minutes and left to stand for 20 minutes. After removal of the aqueous phase (pH 7–7.5) the organic phase was concentrated under reduced pressure. After approximately 4200 ml of toluene had distilled off a viscous oil remained, whereupon an argon atmosphere was applied and the internal temperature was increased to 45°.

At a constant external temperature of 70°, 2000 ml of hexane were added in such a manner that the internal temperature was always 50°–55°. The resulting clear yellow solution was then cooled not too rapidly (20°/hr.) to −10° and stirred at −10° for 1 hour, whereupon the separated crystals were filtered off under suction. In order to remove material remaining in the flask, 1000 ml of hexane were added and stirred vigorously at −10°; the cold suspension was used to wash the filter cake. There were obtained 578 g (66%) of benzyl 3(S)-(t-butylcarbamoyl)-1,2,3,4-tetrahydro-2-isoquinolinecarboxylate in the form of whitish crystals of melting point 105°–106°, purity (according to HPLC) 99.0%, $[\alpha]_D^{20} = -34.2°$ (c=1 in methanol).

EXAMPLE 2

5.7 kg of benzyl 3(S)-(t-butylcarbamoyl)-1,2,3,4-tetrahydro-2-isoquinolinecarboxylate were dissolved in 40 l of ethanol and hydrogenated in an autoclave in the presence of 1.1 kg of 10% palladium-charcoal at a pressure of 10 bar and an internal temperature of 20°–25°. After approximately 2 hours the hydrogen uptake ceased, whereupon the content of the autoclave was filtered, the autoclave and the filter residue were each rinsed twice with 20 l of ethanol each time and the combined filtrates were evaporated, whereby approximately 3.6 kg of crude N-t-butyl-1,2,3,4-tetrahydro-3(S)-isoquinoline-carboxamide were obtained as a beige solid.

40 l of hexane were added to this crude product, the mixture was stirred, heated to approximately 65° (internal temperature), filtered and rinsed twice with 15 l of hot (60°) hexane each time. Subsequently, approximately 35 l of hexane were distilled off, whereupon the mixture was left to cool to room temperature overnight, the separated crystals were filtered off under suction and washed portionwise with a total of 10 l of hexane and 10 l of pentane. After drying in a vacuum at 40° there were obtained 2.9 kg (79%) of N-t-butyl-1,2,3,4-tetrahydro-3(S)-isoquinolinecarboxamide in the form of white crystals having a melting point of 95°–96°, purity (according to GC) 99.6%, $[\alpha]_{589}^{20} = -109.5°$ (c=1 in methanol).

EXAMPLE 3

15 kg of N-t-butyl-1,2,3,4-tetrahydro-3(S)-isoquinoline-carboxamine was suspended in 100 l of ethyl acetate and hydrogenated in the presence of 3 kg of rhodium/Alox (5%) while stirring at a pressure of 80 bar and at an internal temperature of 80°. After approximately 4 hours the hydrogen uptake ceased, whereupon the reaction mixture was filtered, the filter residue was rinsed with 40 l of ethyl acetate and the combined filtrates were evaporated to dryness in a vacuum. After taking up the residue in 40 l of hexane, trituration and evaporation there were obtained 15.3 kg of crude N-t-butyl-decahydro-(4aS,8aS)-isoquinoline-3(S)-carboxamide in the form of a yellow crystallizate.

45 l of hexane were added to this crude product, the mixture was stirred, heated to 65° (internal temperature), filtered and rinsed firstly with 20 l and then with 10 l of hot (60°) hexane. Subsequently, approximately 30 l of hexane were distilled off, whereupon the mixture was cooled to 0° overnight, the separated crystals were removed by centrifugation and rinsed with 10 l of cold (0°) hexane. The resulting moist product (12 kg) was treated with 110 l of hexane, whereupon it was stirred, heated to 65° (internal temperature), filtered and then cooled to 0° overnight. The separated crystals were removed by centrifugation, rinsed with 10 of cold (0°) hexane and dried at 40° in a vacuum. There were obtained 9.1 kg (59%) of N-t-butyl-decahydro-(4aS,8aS)-isoquinoline-3(S)-carboxamide in the form of white crystals of melting point 112°–114°, purity (according to GC) almost 100%, $[\alpha]_{589}^{20} = -73°$ to $-74.2°$ (c=0.5 in methanol).

We claim:

1. A process for the manufacture of 1,2,3,4-tetrahydro-2-isoquinoline derivatives of the formula

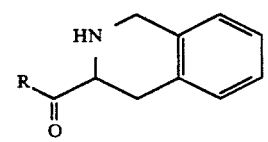

I wherein R signifies hydroxy, lower alkylamino, lower alkoxy or phenyl-C$_{(2-6)}$-alkoxy, the phenyl group can be substituted with one or more lower alkyl or lower alkoxy groups,
which process comprises reacting a phenethylamine derivative of the formula

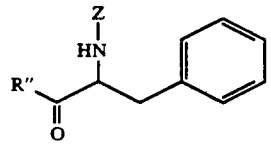   IV wherein Z signifies benzyloxycarbonyl and R" signifies hydroxy, lower alkylamino, lower alkoxy or phenyl-lower-alkoxy, the phenyl group can be further substituted with one or more lower alkyl or lower alkoxy groups, in an inert solvent
with formaldehyde in the presence of sulphuric acid in acetic acid at a temperature between about room temperature and about 50° C. to produce

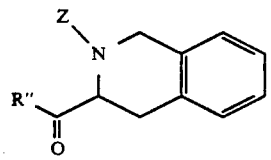   V and cleaving off the group Z in the compound of formula V to form the compound of formula I.

2. The process according to claim 1, wherein R signifies lower alkylamino.

3. The process according to claim 1, wherein the formaldehyde is in the form of either aqueous formaldehyde, paraformaldehyde or a formaldehyde acetal.

4. The process according to claim 2, wherein the formaldehyde is in the form of either aqueous formaldehyde, paraformaldehyde or a formaldehyde acetal.

5. The process according to claim 3, wherein the formaldehyde acetal is dimethoxymethane.

6. The process according to claim 6, wherein toluene is an excess of acetic acid is used as the solvent.

7. The process according to claim 6, wherein toluene is used as the solvent.

8. The process according to claim 1, wherein the phenethylamine derivative of formula IV is reacted in toluene with 3 molar equivalents of dimethoxymethane and 2 molar equivalents of 7.2M sulphuric acid in acetic acid for 24 to 25 hours at about 40° C.

9. The process according to claim 1, wherein the group Z is cleaved off by hydrogenolysis.

10. The process according to claim 9, wherein the cyclization product of formula V is hydrogenated in the presence of a palladium catalyst.

11. A process for the manufacture of 1,2,3,4-tetrahydro-2-isoquinoline derivatives of the formula

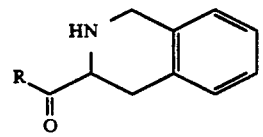   I wherein R signifies lower alkylamino,
which process comprises reacting a phenethylamine derivative of the formula

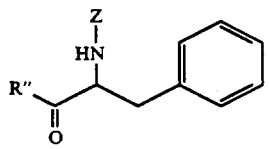   IV wherein Z signifies benzyloxycarbonyl and R" signifies lower alkylamino,
in toluene with 3 molar equivalents of dimethoxymethane and 2 molar equivalents of 7.2M sulphuric acid in acetic acid for 24 to 25 hours at about 40° C. to produce a compound of the formula

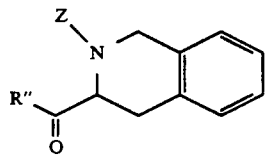   V and cleaving off the group Z by hydrogenolysis to form the compound of formula I.

* * * * *